United States Patent
Nam et al.

(10) Patent No.: US 10,669,340 B2
(45) Date of Patent: Jun. 2, 2020

(54) ANTIBODY AGAINST EGFRVIII AND USE THEREOF

(71) Applicant: SAMSUNG LIFE PUBLIC WELFARE FOUNDATION, Seoul (KR)

(72) Inventors: Do-Hyun Nam, Seoul (KR); Hyunkyu Park, Seoul (KR)

(73) Assignee: SAMSUNG LIFE PUBLIC WELFARE FOUNDATION, Seoul (KR)

(*) Notice: Subject to any disclaimer, the term of this patent is extended or adjusted under 35 U.S.C. 154(b) by 0 days.

(21) Appl. No.: 16/073,787

(22) PCT Filed: Feb. 15, 2017

(86) PCT No.: PCT/KR2017/001623
§ 371 (c)(1),
(2) Date: Jul. 29, 2018

(87) PCT Pub. No.: WO2017/142294
PCT Pub. Date: Aug. 24, 2017

(65) Prior Publication Data
US 2019/0031761 A1 Jan. 31, 2019

(30) Foreign Application Priority Data

Feb. 15, 2016 (KR) .................. 10-2016-0017118
Feb. 15, 2017 (KR) .................. 10-2017-0020416

(51) Int. Cl.
| | | |
|---|---|---|
| C07K 16/28 | (2006.01) | |
| A61K 39/00 | (2006.01) | |
| C12N 15/63 | (2006.01) | |
| A61K 47/68 | (2017.01) | |
| G01N 33/574 | (2006.01) | |
| A61P 35/00 | (2006.01) | |

(52) U.S. Cl.
CPC ...... *C07K 16/2863* (2013.01); *A61K 47/6819* (2017.08); *A61K 47/6849* (2017.08); *A61P 35/00* (2018.01); *C12N 15/63* (2013.01); *G01N 33/574* (2013.01); *G01N 33/57492* (2013.01); *A61K 2039/505* (2013.01); *C07K 2317/14* (2013.01); *C07K 2317/21* (2013.01); *C07K 2317/34* (2013.01); *C07K 2317/56* (2013.01); *C07K 2317/565* (2013.01); *C07K 2317/567* (2013.01); *C07K 2317/622* (2013.01); *C07K 2317/73* (2013.01); *C07K 2317/76* (2013.01); *C07K 2317/92* (2013.01); *G01N 2333/71* (2013.01)

(58) Field of Classification Search
None
See application file for complete search history.

(56) References Cited

U.S. PATENT DOCUMENTS

2005/0222059 A1  10/2005  Tang

FOREIGN PATENT DOCUMENTS

| JP | 2003523771 A | 8/2003 |
|---|---|---|
| JP | 2003523771 T5 | 8/2003 |
| JP | 2007297398 A | 11/2007 |
| KR | 20120098932 A | 9/2012 |
| KR | 20140091064 A | 7/2014 |
| WO | 8801649 A1 | 3/1988 |
| WO | 8806630 A1 | 9/1988 |
| WO | 8807085 A1 | 9/1988 |
| WO | 8807086 A1 | 9/1988 |
| WO | 8809344 A1 | 12/1988 |
| WO | WO0162931 A2 | 8/2001 |

OTHER PUBLICATIONS www.blast.ncbi.nlm.nih.gov-blast,pdf (visited Jul. 25, 2018).
www.uniprot.org,pdf (visited Jul. 25, 2018).
Gupta, P., et al., "Development of an EGFRvIII Specific Recombinant Antibody", "BMC Biotechnology", 2010, pp. 1-13, vol. 10, No. 72.
Wikstrand, C., et al., "Monoclonal Antibodies Against EGFRIII are Tumor Specific and React with Breast and Lung Carcinomas and Malignant Gliomas", "Cancer Research", 1995, pp. 3140-3148, vol. 55, No. 14.
Wikstrand, C., et al., "The Class III Variant of the Epidermal Growth Factor Receptor (EGFRvIII): Characterization and Utilization as an Immunotherapeutic Target", "Journal of NeuroVirology", 1998, pp. 148-158, vol. 4, No. 2.
Dondelinger, M., et al., "Understanding the Significance and Implications of Antibody Numbering and Antigen-Binding Surface/Residue Definition", "Frontiers in Immunology", Oct. 16, 2018, Page(s) doi:10.3389/fimmu.2018.02278, vol. 9, No. Article 2278.
Rudikoff, Stuart, et al., "Single Amino Acid Substitution Altering Antigen-Binding Specificity", "Proc. Natl. Acad. Sci. USA", Mar. 15, 1982, pp. 1979-1983, vol. 79, No. 6.

*Primary Examiner* — Marianne P Allen
(74) *Attorney, Agent, or Firm* — Hultquist, PLLC; Steven J. Hultquist

(57) ABSTRACT

The present invention relates to an antibody or antigen-binding fragment thereof against EGFRvIII (Epidermal Growth Factor Receptor Variant III), a nucleic acid encoding the same, a vector comprising the nucleic acid, a cell transformed with the vector, a method for producing the antibody or antigen-binding fragment thereof, a composition for preventing or treating cancer, which comprises the same, a composition for diagnosing cancer, which comprises the same, and a kit for diagnosing cancer, which comprise the composition for diagnosing cancer.

6 Claims, 7 Drawing Sheets
(7 of 7 Drawing Sheet(s) Filed in Color)
Specification includes a Sequence Listing.

ANTIBODY AGAINST EGFRVIII AND USE THEREOF

CROSS-REFERENCE TO RELATED APPLICATIONS

This is a U.S. national phase under the provisions of 35 U.S.C. § 371 of International Patent Application No. PCT/KR17/01623 filed Feb. 15, 2017, which in turn claims priority of Korean Patent Application No. 10-2016-0017118 filed Feb. 15, 2016 and Korean Patent Application No. 10-2017-0020416 filed Feb. 15, 2017. The disclosures of such international patent application and Korean priority patent applications are hereby incorporated herein by reference in their respective entireties, for all purposes.

TECHNICAL FIELD

The present invention relates to an antibody or antigen-binding fragment thereof against EGFRvIII (Epidermal Growth Factor Receptor Variant III), a nucleic acid encoding the same, a vector comprising the nucleic acid, a cell transformed with the vector, a method for producing the antibody or antigen-binding fragment thereof, and a composition for preventing or treating cancer, which comprise the same, a composition for diagnosing cancer, which comprise the same, and a kit for diagnosing cancer, which comprise the composition for diagnosing cancer.

BACKGROUND ART

The use of monoclonal antibodies for cancer treatment has been quite successful. Antibody-drug conjugates have become potent new therapeutic options for the treatment of lymphoma and solid tumors, and immunoregulatory antibodies have recently demonstrated considerable success in clinical trials. The development of therapeutic antibodies is based on a deep understanding of cancer biology, protein engineering techniques, mechanisms of drug resistance, and the interaction between the immune system and cancer cells.

Antigens expressed on the surfaces of human cancer cells mean a broad range of targets that are overexpressed relative to normal tissues or mutated and selectively expressed. The key problem is to identify antigens appropriate for antibody-based therapies. These therapies mediate changes in ligand or receptor function (i.e., function as agonists or antagonists), regulate the immune system by antibody-dependent cell cytotoxicity (ADCC), and deliver a specific drug bound to a specific antibody that targets a specific antigen, thereby exhibiting their efficacy. Molecular techniques that can change antibody pharmacokinetics, activity, function, size and immunostimulatory activity have emerged as key elements in the development of new antibody-based therapies. Evidence from clinical trials of therapeutic antibodies directed against cancer patients emphasizes the importance of the binding affinities of antibodies for target antigens, the selection of antibody structures, and approaches for the selection of optimized antibodies, including therapeutic approaches (signaling inhibition or immune function).

In connection with this, studies on antibodies against epidermal growth factor receptor (EGFR) antigen have been conducted. The EGFR is the 170 kilodalton membrane lipoprotein product of the proto-oncogene c-erb B. The sequence of the EGFR gene is known. The EGFR gene is the cellular homolog of the erb-B oncogene originally identified in avian erythroblastasis viruses. Activation of this oncogene by gene amplification has been observed in a variety of human tumors.

EGFR is overexpressed on various types of human solid tumors. EGFR overexpression has been observed in certain lung, breast, colon, gastric, brain, bladder, head and neck, ovarian, kidney and prostate carcinomas. Both epidermal growth factor (EGF) and transforming growth factor-alpha (TGF-alpha) have been demonstrated to bind to EGFR and to lead to cellular proliferation and tumor growth. In addition, amplification, point mutations and splice variants of EGFR have been reported in several human cancers.

EGFR variants are caused by gene rearrangement accompanied by EGFR gene amplification. There are eight major variants of EGFR that are known: (i) EGFRvI lacks a majority of the extracellular domain of EGFR, (ii) EGFRvII consists of an 83 aa in-frame deletion in the extracellular domain of EGFR, (iii) EGFRvIII consists of a 267 aa in-frame deletion in the extracellular domain of EGFR, (iv) EGFRvIV contains deletions in the cytoplasmic domain of EGFR, (v) EGFRvV contains deletions in cytoplasmic domain of EGFR, (vi) EGFR.TDM/2-7 contains a duplication of exons 2-7 in the extracellular domain of EGFR, (vii) EGFR.TDM/18-25 contains a duplication of exons 18-26 in the extracellular domain of EGFR, and (viii) EGFR.TDM/18-26 contains a duplication of exons 18-26 in the tyrosine kinase domain of EGFR. In addition, there is a second, more rare, EGFRvIII mutant (EGFRvIII/AΔ12-13) that possesses a second deletion that introduces a novel histidine residue at the junction of exons 11 and 14.

EGFRvIII is the most commonly occurring variant of the epidermal growth factor (EGF) receptor in human cancers, and is expressed in about 30% of glioblastoma multiforme (GBM) patients, but is not expressed in normal tissue. This variant of the EGF receptor contributes to tumor progression through constitutive signaling in a ligand independent manner.

Mutations or rearrangements in genes that potentially drive neoplasia can be identified in many cancers. Results have shown that oncogenic proteins can contribute to cancer stem cell-related pathways. It stands to reason that the products of such altered genes could be used to identify and potentially target cancer stem cells. In practice, this approach has been difficult to establish because driver mutations are present in cells throughout the mass and typically are not specific to any subpopulation. Thus, mutant proteins may not have any direct role in cancer stem cells and generally potentiate tumor growth. In addition, most altered proteins are intracellular.

The correlation between mutant proteins and cancer stem cells is not clear. Glioblastoma tumors are known to frequently express EGFRvIII, an EGFR variant expressed through gene rearrangement and amplification. Since tyrosine phosphorylation sites are always present in an activated form, they show strong tumorigenicity. However, despite this modification, the expression of EGFRvIII is limited. In cancer stem cells, EGFRvIII is highly expressed with CD133, and EGFRvIII+/CD133+ cells have high regeneration and tumor initiation capability. EGFRvIII+ cells were associated with stem/precursor markers, whereas differentiation markers were found in EGFRvIII− cells. Expression of EGFRvIII was lost in normal cell culture, but maintained in tumor sphere culture. In addition, cultured cells simultaneously express EGFRvIII+/CD133+, and are regenerated, and have tumor-initiating ability.

In order to treat cancer that overexpresses EGFRvIII, an anti-EGFRvIII antibody is required which is capable of binding to EGFRvIII with high affinity and inhibiting the growth of cancer cells.

Antibody therapeutic agents such as Cetuximab, which bind specifically to EGFR, have been developed conventionally. However, these antibody therapeutic agents entail problems that antigen specificity for EGFRvIII mutant cancer cells is very low, and that the inhibition of cancer cell growth does not appear.

Under this technical background, the present inventors have made extensive efforts to develop an anticancer therapeutic antibody that binds specifically to EGFRvIII. As a result, the present inventors have developed an anti-EGFRvIII antibody, which binds to EGFRvIII with high affinity, by using phage display technology, and have found that this anti-EGFRvIII antibody can significantly inhibit migration of cancer cells, thereby completing the present invention.

DISCLOSURE OF INVENTION

Technical Problem

It is an object of the present invention to provide a novel antibody or antigen-binding fragment thereof against EGFRvIII.

Another object of the present invention is to provide a nucleic acid encoding the above-described antibody or antigen-binding fragment thereof.

Still another object of the present invention is to provide a vector comprising the above-described nucleic acid, a cell transformed with the above-described vector, and a method of producing the above-described antibody or antigen-binding fragment thereof.

Yet another object of the present invention is to provide a composition for preventing or treating cancer, which comprises the above-described antibody or antigen-binding fragment thereof.

A further object of the present invention is to provide a composition for diagnosing cancer, which comprises the above-described antibody or antigen-binding fragment thereof, and a kit for diagnosing cancer, which comprises the above-described composition.

Technical Solution

To achieve the above object, the present invention provides an antibody or antigen-binding fragment thereof against EGFRvIII (Epidermal Growth Factor Receptor Variant III), in which the antibody or antigen-binding fragment thereof is one that binds to an EGFRvIII epitope having a sequence of SEQ ID NO: 1.

The present invention also provides a nucleic acid encoding a heavy chain variable region of the above-described antibody or antigen-binding fragment thereof.

The present invention also provides a vector comprising the above-described nucleic acid.

The present invention also provides a cell transformed with the above-described vector.

The present invention also provides a method of producing the above-described antibody or antigen-binding fragment thereof, the method comprising the steps of: (a) culturing the above-described cell; and (b) recovering an antibody or antigen-binding fragment thereof from the cultured cell.

The present invention also provides a composition for preventing or treating cancer, which comprises the above-described antibody or antigen-binding fragment thereof as an active ingredient.

The present invention also provides a composition for diagnosing cancer, which comprises the above-described antibody or antigen-binding fragment thereof.

The present invention also provides a kit for diagnosing cancer, which comprises the above-described composition for diagnosing cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
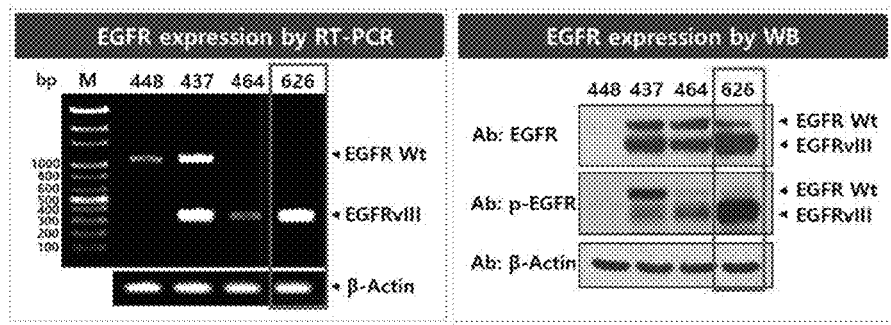
FIG. 1 shows the results of RT-PCR (Reverse Transcription Polymerase Chain Reaction) and Western blot analysis performed to analyze mutations and expression levels of EGFRvIII in glioblastoma multiforme (GBM) patient-derived cells.

Unless defined otherwise, all the technical and scientific terms used herein have the same meaning as those generally understood by one of ordinary skill in the art to which the invention pertains. Generally, the nomenclature used herein and the experiment methods, which will be described below, are those well-known and commonly employed in the art.

In one aspect, the present invention is directed to an antibody or antigen-binding fragment thereof against EGFRvIII, in which the antibody or antigen-binding fragment thereof is one that binds to an EGFRvIII epitope having a sequence of SEQ ID NO: 1.

The present inventors have made extensive efforts to develop an anticancer therapeutic antibody that binds to EGFRvIII known to be expressed in various cancers. As a result, the present inventors have produced an anti-EGFRvIII antibody, which binds to EGFRvIII with high affinity and is internalized into cells, by use of phage display technology, and have found that this anti-EGFRvIII antibody can significantly inhibit cancer cell migration.

As used herein, the term "EGFRvIII" refers to a mutant type of epidermal growth factor receptor, which is recognized by MR1 scFv and characterized by an 801 bp in-frame deletion of exons 2-7 near the amino terminus. It appears that EGFRvIII is highly expressed in about 50-60% of glioblastoma and present in about 70-80% of breast and ovarian carcinomas and about 16% of non-small cell lung carcinomas. The mutant receptor is expressed on the cell surface and produces a new tumor-specific cell surface epitope at deletion junctions.

As used herein, "epitope" refers to a protein determinant capable of specifically binding to an antibody. Epitopes usually comprise chemically active surface groupings of molecules such as, for example, amino acids or sugar side chains, and usually have specific three dimensional structural characteristics, as well as specific charge characteristics. Conformational and nonconformational epitopes are distinguished in that the binding to the former but not the latter is lost in the presence of denaturing solvents. The present invention is directed to an antibody against an EGFRvIII epitope having a sequence of SEQ ID NO: 1 or an antigen-binding fragment thereof.

As used herein, "antibody" refers to an anti-EGFRvIII antibody that specifically binds to EGFRvIII. The scope of the present invention also includes an intact antibody form that specifically binds to EGFRvIII as well as an antigen-binding fragment of the antibody molecule.

The complete antibody is a structure having two full-length light chains and two full-length heavy chains, and each light chain is linked by a disulfide bond with a heavy chain. A constant region of the heavy chain has gamma ($\gamma$), mu ($\mu$), alpha ($\alpha$), delta ($\delta$), and epsilon ($\epsilon$) types. Subclasses have gamma 1 ($\gamma$1), gamma 2 ($\gamma$2), gamma 3 ($\gamma$3), gamma 4 ($\gamma$4), alpha 1 ($\alpha$1), and alpha 2 ($\alpha$2) types. A constant region of the light chain has kappa ($\kappa$) and lambda ($\lambda$) types.

In the present invention, the antibody includes monoclonal antibodies, multispecific antibodies, human antibodies, humanized antibodies, chimeric antibodies, single-chain Fvs (scFV), single chain antibodies, Fab fragments, F(ab') fragments, disulfide-linked Fvs (sdFV) and anti-idiotype (anti-Id) antibodies, and epitope-binding fragments of these antibodies, but is not limited thereto.

An antigen binding fragment or an antibody fragment of an antibody refers to a fragment having an antigen binding function and includes Fab, F(ab'), F(ab')2, Fv, and the like. Fab of the antibody fragments has a structure including variable regions of a light chain and a heavy chain, a constant region of the light chain, and a first constant region (CH1) of the heavy chain with one antigen-binding site. Fab' differs from Fab in that it has a hinge region containing one or more cysteine residues at the C-terminal of the heavy chain CH1 domain. The F(ab')2 antibody is produced when the cysteine residue of the hinge region of the Fab' forms a disulfide bond. Recombinant techniques for generating Fv fragments with minimal antibody fragments having only a heavy chain variable region and a light chain variable region are described in PCT International Publication Nos. WO88/10649, WO88/106630, WO88/07085, WO88/07086, and WO88/09344. A two-chain Fv has a non-covalent bonding between a heavy chain variable region and a light chain variable region. A single chain Fv (scFv) is connected to a heavy chain variable region and a light chain variable region via a peptide linker by a covalent bond or directly at the C-terminal. Thus, the single chain Fv (scFv) has a structure such as a dimer like the two-chain Fv. Such an antibody fragment can be obtained using a protein hydrolyzing enzyme (for example, when the whole antibody is cleaved with papain, Fab can be obtained, and when whole antibody is cut with pepsin, F(ab')2 fragment can be obtained), and it can also be produced through gene recombinant technology.

An "Fv" fragment is an antibody fragment that contains complete antigen recognition and binding sites. Such region includes a heavy chain variable domain and a light chain variable domain, for example, dimers substantially tightly covalently associated with scFv.

"Fab" fragment contains the variable and constant domain of the light-chain and the variable and first constant domain (CH1) of the heavy chain. F(ab')2 antibody fragment generally includes a pair of Fab fragments covalently linked by hinge cysteine near their carboxy-terminus.

"Single chain Fv" or "scFv" antibody fragment comprises VH and VL domains of the antibody. Such domains are within a single polypeptide chain. The Fv polypeptide may further include a polypeptide linker between the VH domain and the VL domain such that the scFv can form the desired structure for antigen binding.

In one embodiment, an antibody according to the present invention is in the form of an Fv (e.g. scFv) or a complete antibody form. Further, the heavy chain constant region can be selected from any one isotype of gamma ($\gamma$), mu ($\mu$), alpha ($\alpha$), delta ($\delta$), and epsilon ($\epsilon$). For example, the constant region is gamma 1 (IgG1), gamma 3 (IgG3), or gamma 4 (IgG4). The light chain constant region may be kappa or lambda types.

The term "heavy chain" as used herein refers to a full-length heavy chain and fragments thereof including a variable region domain VH including an amino acid sequence with sufficient variable region sequence to confer specificity to an antigen and three constant region domains CH1, CH2, and CH3. The term "light chain" as used herein refers to a full-length heavy chain and fragments thereof including a variable region domain VL including an amino acid sequence with sufficient variable region sequence to confer specificity to an antigen and a constant region domain CL.

The monoclonal antibody refers to an antibody obtained from a substantially homogeneous population of antibodies, i.e., the same except for possible naturally occurring mutations that may be present in trace amounts of individual antibodies that occupy the population. The monoclonal antibody is highly specific and is derived against a single antigenic site.

The non-human (e.g. murine) antibody of the "humanized" form is a chimeric antibody containing minimal sequence derived from non-human immunoglobulin. In most cases, the humanized antibody is a human immunoglobulin (receptor antibody) that has been replaced by a residue from the hypervariable region of a non-human species (donor antibody), such as a mouse, rat, rabbit, and non-human primate, having specificity, affinity, and ability to retain a residue from the hypervariable region of the receptor.

"Human antibody" is a molecule derived from human immunoglobulin and means that all of the amino acid sequences constituting the antibody including the complementarity determining region and the structural region are composed of human immunoglobulin.

A heavy chain and/or light chain is partly identical or homologous to the corresponding sequence in an antibody derived from a particular species or belonging to a particular antibody class or subclass, while the remaining chain(s) are identical or homologous to corresponding sequences in an antibody derived from another species or belonging to another antibody class or subclass "chimeric" antibodies (immunoglobulins) as well as a fragment of such antibody exhibiting the desired biological activity.

"Antibody variable domain" as used herein refers to the light and heavy chain regions of an antibody molecule including the amino acid sequences of a complementarity determining region (CDR; i.e., CDR1, CDR2, and CDR3) and a framework region (FR). VH refers to a variable domain of the heavy chain. VL refers to a variable domain of the light chain.

"Complementarity determining region" (CDR; i.e., CDR1, CDR2, and CDR3) refers to the amino acid residue of the antibody variable domain, which is necessary for antigen binding. Each variable domain typically has three CDR regions identified as CDR1, CDR2, and CDR3.

"Framework region" (FR) is a variable domain residue other than a CDR residue. Each variable domain typically has four FRs identified as FR1, FR2, FR3, and FR4.

In one embodiment, the present invention provides an antibody or antigen-binding fragment thereof including a heavy chain CDR (complementarity determining region) and a light chain CDR as followings: a heavy chain variable region comprising complementarity determining region (CDR) H1 comprising a sequence of SEQ ID NO: 2, CDRH2 comprising a sequence of SEQ ID NO: 3, and CDRH3 comprising a sequence of SEQ ID NO: 4; and a light chain variable region comprising CDRL1 comprising the sequence of SEQ ID NO: 5, CDRL2 comprising the sequence of SEQ ID NO: 6, and CDRL3 comprising the sequence of SEQ ID NO: 7.

In one embodiment, the antibody or antigen-binding fragment thereof of the present invention may comprise a framework region (FR) comprising one or more sequences selected from the group consisting of sequences of SEQ ID NOS: 8 to 15. Specifically, the antibody or antigen-binding fragment thereof may comprise a heavy chain variable region comprising a heavy chain framework region (FR) comprising one sequence selected from the group consisting of sequences of SEQ ID NOS: 8 to 11.

In this case, the heavy chain variable region may comprise a heavy chain FR1 comprising a sequence of SEQ ID NO: 8, a heavy chain FR2 comprising a sequence of SEQ ID NO: 9, a heavy chain FR3 comprising a sequence of SEQ ID NO: 10, or a heavy chain FR4 comprising a sequence of SEQ ID NO: 11.

In addition, the antibody or antigen-binding fragment thereof of the present invention may comprise a light chain variable region comprising a light chain framework region (FR) comprising one sequence selected from the group consisting of sequences of SEQ ID NOS: 12 to 15.

In this case, the light chain variable region may comprise a light chain FR1 comprising a sequence of SEQ ID NO: 12, a light chain FR2 comprising a sequence of SEQ ID NO: 13, a light chain FR3 comprising a sequence of SEQ ID NO: 14, or a light chain FR4 comprising a sequence of SEQ ID NO: 15.

In one embodiment, the antibody or antigen-binding fragment thereof of the present invention may comprise a heavy chain variable region comprising a sequence of SEQ ID NO: 16 and/or a light chain variable region comprising a sequence of SEQ ID NO: 17.

"Phage display" is a technique for displaying a fusion protein by fusing a mutant polypeptide and at least a part of a coat protein on a surface of phase such as a fibrous phage particle. The phage display is useful for targeting a large library of randomized protein variants to quickly and efficiently classify sequences that bind to target antigens in high affinity. Displaying peptides and protein libraries on phage has been used to screen millions of polypeptides to identify polypeptides with specific binding properties.

The phage display technique has provided a powerful tool for generating and screening novel proteins that bind to specific ligands (e.g., antigens). Using the phage display technique, a large library of protein variants can be generated and sequences binding to the target antigens in high affinity can be quickly classified. The nucleic acid encoding the mutant polypeptide is fused with a nucleic acid sequence encoding a viral coat protein, e.g., a gene III protein or a gene VIII protein. A monovalent phage display system has been developed in which a nucleic acid sequence encoding a protein or polypeptide is fused with a nucleic acid sequence encoding a part of the gene III protein. In the monovalent phage display system, the gene fusion is expressed at a low level, and the wild-type gene III protein is also expressed, thereby maintaining the infectivity of the particles.

Demonstrating the expression of peptides on the fibrous phage surface and the expression of functional antibody fragments in the peripheral cytoplasm of E. coli is important in developing antibody phage display libraries. Libraries of antibodies or antigen-binding polypeptides have been prepared in a number of ways, for example by altering a single gene by inserting a random DNA sequence or by cloning a related genic line. The library can be screened for expression of antibodies or antigen binding proteins with the desired characteristics.

The phage display technique has several advantages over conventional hybridomas and recombinant methods for producing antibodies with the desired characteristics. This technique allows the generation of a large antibody library having various sequences in a short time without the use of animals. The production of hybridomas or humanized antibodies may take several months to manufacture. Further, the phage antibody library may produce antibodies against antigens that are toxic or have low antigenicity since no immunity is required. The phage antibody library can also be used to generate and identify novel therapeutic antibodies.

A technology can be used in which human antibodies are generated from virgin B-cell Ig repertoires or human germ-line sequences immunized or non-immunized using a phage display library. Various lymphatic tissues may be used to prepare virgin or non-immune antigen-binding libraries.

Techniques for identifying and separating high affinity antibodies from a phage display library are important for separating new therapeutic antibodies. The separation of high affinity antibodies from the library may depend on the size of the library, production efficiency in bacterial cells, and library diversity. The size of the library is reduced by inefficient production due to improper folding of an antibody or antigen binding protein and the presence of the stop codon. Expression in bacterial cells can be inhibited when an antibody or antigen binding domain is not properly folded. The expression can be increased by alternately mutating residues on a surface of a variable/constant interface or selected CDR residues. A sequence of the framework region is one element to provide appropriate folding when antibody phage libraries are generated in bacterial cells.

It is important to generate various libraries of an antibody or antigen binding proteins in high affinity antibody separation. The CDR3 region has been found to often participate in antigen binding. The CDR3 region on a heavy chain varies considerably in terms of size, sequence, and structural steric conformation so that various libraries can be prepared using the CDR3 region.

Further, diversity may be generated by randomizing the CDR regions of the variable heavy and light chains using all 20 amino acids at each position. The use of all 20 amino acids results in an increased variability of variant antibody sequences and an increased chance of identifying new antibodies.

An antibody or antibody fragment of the present invention may include, within the scope of specifically recognizing EGFRvIII, the sequence of the anti-EGFRvIII antibody of the present invention described herein as well as biological equivalents thereof. The amino acid sequence of the antibody may be additionally modified to further improve the binding affinity and/or other biological properties of the antibody. Such modifications include, for example, deletion, insertion and/or substitution of the amino acid sequence residues of the antibody. Such amino acid variations are made based on the relative similarity of amino acid side chain substituents, such as hydrophobicity, hydrophilicity, charge, and size. By analysis of the size, shape and type of amino acid side chain substituents, it is recognized that each of arginine, lysine and histidine is a positively charged residue; alanine, glycine and serine have similar sizes; and phenylalanine, tryptophan and tyrosine have similar shapes. Based on these considerations, it is thus found that arginine, lysine and histidine; alanine, glycine and serine; and phenylalanine, tryptophan and tyrosine, respectively, are biologically functional equivalents.

On introduction of mutations, the hydropathic index of amino acids can be considered. Each amino acid is assigned a hydrophobic index according to its hydrophobicity and charge: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The hydrophobic amino acid index is very important in imparting the interactive biological function of proteins. It is well known that substitution with an amino acid having a similar hydrophobic index can retain similar biological activities. When a mutation is introduced with reference to a hydrophobic index, the substitution is made between amino acids showing a hydrophobic index difference preferably within ±2, more preferably within ±1, even more preferably within ±0.5.

Meanwhile, it is also well known that the substitution between amino acids with similar hydrophilicity values leads to proteins with equivalent biological activity. As disclosed in U.S. Pat. No. 4,554,101, the following hydrophilicity values are assigned to each amino acid residue: arginine (+3.0); lysine (+3.0); aspartate (+3.0±1); glutamate (+3.0 ±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4).

Amino acid substitution in proteins that do not totally alter the activity of the molecule is known in the art (H. Neurath, R. L. Hill, The Proteins, Academic Press, New York, 1979). The substitution occurs the most commonly between amino acid residues, e.g., Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly.

Considering the mutation having the above-mentioned biological equivalent activity, the antibody of the present disclosure or the nucleic acid molecule encoding the same is interpreted to include a sequence showing substantial identity with the sequence described in the sequence listing. The substantial identity means a sequence showing at least 61% homology, more preferably 70% homology, even more preferably 80% homology, and most preferably 90% homology by aligning the sequence of the present disclosure with any other sequence as much as possible and analyzing the aligned sequence using algorithms commonly used in the art. Alignment methods for sequence comparison are well known in the art. NCBI Basic Local Alignment Search Tool (BLAST) may be accessible from, e.g., NBCI and can be used in association with sequence analysis programs such as blastp, blasm, blastx, tblastn and tblastx on the Internet. BLSAT is available at www.ncbi.nlm nih.gov/BLAST/. A comparison of sequence homology using this program can be found at www.ncbi.nlm.nih.gov/BLAST/blast_help.html.

In another aspect, the present invention is directed to a nucleic acid encoding the antibody or antigen-binding fragment thereof.

The antibody or antigen-binding fragment thereof of the present invention may be recombinantly produced by isolating the nucleic acid encoding an antibody or antigen-binding fragment thereof of the present invention. The nucleic acid is isolated and inserted into a cloneable vector to result in further cloning (amplification of DNA) or further expression. Based on this, in still another aspect, the present invention is directed to a vector including the nucleic acid.

"Nucleic acid" has a broad meaning including DNA (gDNA and cDNA) and RNA molecules. Nucleotides, basic elements of nucleic acids, include natural nucleotides as well as analogues in which sugar or base sites are modified. The sequence of the nucleic acid encoding the heavy and light chain variable regions of the present disclosure may be modified. Such modifications include the addition, deletion, or non-conservative substitution or conservative substitution of nucleotides.

In one embodiment, the nucleic acid encoding a variable region of the antibody or antigen-binding fragment thereof according to the persent invention may comprise a sequence of SDE ID NO: 18 or 19. Here, the nucleic aci encoding a heavy chain variable region may comprise a sequence of SDE ID NO: 18, and the nucleic aci encoding a light chain variable region may comprise a sequence of SDE ID NO: 19.

The nucleic acid of the present disclosure is interpreted to include a nucleotide sequence that exhibits substantial identity to the nucleotide sequence. The substantial identity means a nucleotide sequence showing at least 80% homology, more preferably at least 90% homology, and most preferably at least 95% homology by aligning the nucleotide sequence of the present invention with any other sequence as much as possible and analyzing the aligned sequence using algorithms commonly used in the art.

The DNA encoding the antibody can be easily separated or synthesized using conventional procedures (for example, using an oligonucleotide probe capable of specifically binding to DNA encoding the heavy chain and the light chain of the antibody). Many vectors are available. Vector components generally include, but are not limited to, one or more of the following: a signal sequence, an origin of replication, one or more marker gene, an enhancer element, a promoter, and a transcription termination sequence.

The term "vector" as used herein, includes a plasmid vector; a cosmid vector; a bacteriophage vector; and a viral vector, e.g., an adenovirus vector, retroviral vectors, and adeno-associated viral vectors as a mean for expressing a target gene in a host cell. The nucleic acid encoding the antibody in the vector is operably linked to a promoter.

"operably linked" is meant a functional linkage between a nucleic acid expression control sequence (e.g., an array of promoter, signal sequence, or transcription regulation factor binding site) and another nucleic acid sequence, thereby controlling the transcription and/or translation of another nucleic acid sequence.

When a prokaryotic cell is used as a host, a strong promoter capable of promoting transcription (such as a tac promoter, lac promoter, lacUV5 promoter, 1pp promoter, pLλ promoter, pRλ promoter, rac5 promoter, amp promoter, recA promoter, SP6 promoter, trp promoter, and T7 promoter), a ribosome binding site for initiation of translation, and a transcription/translation termination sequence are generally included. Further, for example, when a eukaryotic cell is used as a host, a promoter derived from a genome of a mammalian cell (e.g., a metallothionein promoter, a β-actin promoter, a human hemoglobin promoter and a human muscle creatine promoter) or a promoter derived from an mammalian virus (e.g., adenovirus late promoter, vaccinia virus 7.5 K promoter, SV40 promoter, cytomegalovirus (CMV) promoter, HSV tk promoter, mouse mammary tumor virus (MMTV) promoter, HIV LTR promoter, moloney virus promoter, epstein barr virus (EBV) promoter, and Rous sarcoma virus (RSV) promoter) can be used, and generally have a polyadenylation sequence as a transcription termination sequence.

Optionally, the vector may be fused with another sequence in order to facilitate purification of an antibody expressed therefrom. Fused sequences include, for example, glutathione S-transferase (Pharmacia, USA), maltose binding protein (NEB, USA), FLAG (IBI, USA), and 6× His (hexahistidine; Qiagen, USA).

The vector includes an antibiotic resistance gene commonly used in the art as selectable markers, and the resistance gene includes, for example, the genes for ampicillin, gentamycin, carbenicillin, chloramphenicol, streptomycin, kanamycin, geneticin, neomycin and, tetracycline.

In yet another aspect, the present invention is directed to a cell transformed with the above-mentioned vector. The cell used to produce the antibody of the present disclosure may be, but is not limited to, a prokaryote, yeast, or higher eukaryotic cell.

In the present invention, as the transformed cell, the prokaryotic host cell, for example, such as a strain belonging to the genus Bacillus such as *Escherichia coli, Bacillus subtilis,* and *Bacillus thuringiensis, Streptomyces, Pseudomonas* (for example, *Pseudomonas putida*), *Proteus mirabilis,* and *Staphylococcus* (for example, *Staphylococcus carnosus*), can be used.

Meanwhile, interest in animal cells is greatest, and an example of a useful host cell line may be, but is not limited thereto, COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U205, or HT1080.

In a further aspect, the present invention is directed to a method of producing an antibody or antigen-binding fragment thereof, comprising the steps of: (a) culturing the above-described cell; and (b) recovering an antibody or antigen-binding fragment thereof from the cultured cell.

The cells can be cultured in various media. Commercially available media can be used as a culture medium without limitation. All other essential supplements known to those skilled in the art may be included at the appropriate concentrations. Culturing conditions, e.g., temperature and pH have already been used with the selected host cells for expression, which will be apparent to those skilled in the art.

When the antibody or antigen-binding fragment thereof is recovered, impurities can be removed, e.g., by centrifugation or ultrafiltration, and the resultant can be purified, for example, by affinity chromatography. Additional purification techniques may be used, such as anion or cation exchange chromatography, hydrophobic interaction chromatography, and hydroxyl apatite chromatography.

In a still further aspect, the present invention is directed to a composition for preventing or treating cancer, comprising the above-described antibody.

The present invention may be, e.g., a pharmaceutical composition for preventing or treating cancer, comprising (a) a pharmaceutical effective amount of an antibody against EGFRvIII or antigen-binding fragment thereof according to the present invention; and (b) a pharmaceutically acceptable carrier. The present invention is also directed to a method for prevention or treatment of a cancer, comprising administering an effective amount of the antibody against EGFRvIII or antigen-binding fragment thereof according to the present invention to a patient.

Since the composition uses the anti-EGFRvIII antibody or antigen-binding fragment thereof of the present invention as an active ingredient, the descriptions common to both of them are excluded in order to avoid the excessive complexity of the present specification caused by the repeated descriptions.

As demonstrated in Examples as described below, the antibody or antigen-binding fragment thereof of the present invention binds to EGFRvIII with high affinity and thus inhibits the migration of cancer cells overexpressing EGFRvIII, so that it can be used in the prevention and treatment of a cancer.

"Prevention" means any action that inhibits or delays progress of a cancer by administration of a composition according to the present invention, and "treatment" means suppression of development, alleviation, or elimination of a cancer.

"Cancer overexpressing EGFRvIII" refers to a cancer having EGFRvIII on the cancer cell surface at a significantly higher level compared to non-cancerous cells of the same tissue type.

The composition is applied to a disease that is a cancer overexpressing EGFRvIII, for examples, glioblastoma, astrocytoma, glioma, neuroblastoma, testicular cancer, colon cancer, melanoma, pancreatic cancer, lung cancer, breast cancer, esophageal cancer, lung cancer, ovarian cancer, prostate cancer, and squamous cell carcinoma.

In a yet further aspect, the present invention is directed to a composition for inhibiting the metastasis or invasion of cancer cells, which comprises an antibody or antigen-binding fragment thereof against EGFRvIII. The present invention is also directed to a method for inhibiting the metastasis or invasion of cancer cells by treating an antibody or antigen-binding fragment thereof against EGFRvIII.

A pharmaceutically acceptable carrier to be contained in the composition of the present invention is conventionally used in the formulation and includes, but are not limited to, lactose, dextrose, sucrose, sorbitol, mannitol, starch, acacia rubber, calcium phosphate, alginate, gelatin, calcium silicate, microcrystalline cellulose, polyvinylpyrrolidone, water, syrup, methylcellulose, methylhydroxybenzoate, propylhydroxybenzoate, talc, magnesium stearate, mineral oil, and the like. The composition of the present invention may further include, e.g., a lubricant, a wetting agent, a sweetener, a flavoring agent, an emulsifying agent, a suspending agent, and a preservative in addition to the components.

The pharmaceutical composition of the present invention may be administered orally or parenterally. The parenteral administration is carried out by intravenous injection, subcutaneous injection, intramuscular injection, intraperitoneal injection, endothelial administration, topical administration, intranasal administration, intrapulmonary administration, rectal administration, and the like.

Because a protein or peptide is digested when administered orally, a composition for oral administration should be formulated to coat an active drug agent or to be protected against degradation in stomach. Also, the pharmaceutical composition may be administered by any device which can transport active substances to target cells.

The appropriate dosage of the composition according to the present invention may vary depending on factors such as the formulation method, the administration method, patient's age, body weight, sex, pathological condition, food, administration time, route of administration, excretion rate and reaction sensitivity. Thus, a commonly skilled physician can easily determine and prescribe a dosage that is effective for the desired treatment or prophylaxis. For example, the daily dosage of the pharmaceutical composition of the present invention is 0.0001 mg/kg to 100 mg/kg. The term "pharmaceutically effective amount" as used herein refers to an amount sufficient to prevent or treat cancer.

The pharmaceutical composition of the present invention may be formulated using a pharmaceutically acceptable carrier and/or an excipient according to a method which can be easily carried out by those having ordinary skill in the art to which the present invention pertains so as to be provided in a unit dosage form or enclosed into a multi-dose container. Here, the formulations may be in the form of solutions, suspensions or emulsions in oils or aqueous media, or in the form of extracts, grains, suppositories, powders, granules, tablets or capsules, and may additionally include dispersing or stabilizing agents.

The composition of the present invention may be administered as an individual therapeutic agent or in combination with another therapeutic agent, and may be administered sequentially or simultaneously with a conventional therapeutic agent.

In another further aspect, the present invention is directed to a composition for diagnosing cancer, which comprises an antibody against EGFRvIII. The present invention is also directed to a method of diagnosing cancer by treating an antibody or antigen-binding fragment thereof against EGFRvIII.

Cancer can be diagnosed by measuring the expression level of EGFRvIII in a sample by use of the antibody against EGFRvIII according to the present invention. The expression level can be measured according to a conventional immunoassay method. For example, the expression level may be measured using the antibody against EGFRvIII by radioactive immunoassay, radioimmunoprecipitation, immunoprecipitation, immunohistochemical staining, ELISA (enzyme-linked immunosorbent assay), capture-ELISA, inhibition or competition assay, sandwich assay, flow cytometry, immunofluorescent staining, and immunoaffinity purification, but is not limited thereto.

Cancer can be diagnosed by analyzing the intensity of a signal resulting from the immunoassay process. In other words, when the marker protein of the present invention is highly expressed in a biological sample and the signal from the sample is stronger than that from a normal biological sample (e.g., normal gastric tissue, blood, plasma or serum), the sample is diagnosed as cancer.

In another still further aspect, the present invention is directed to a kit for diagnosing cancer, which comprises the above-described composition for diagnosing cancer. The kit according to the present invention includes an antibody against EGFRvIII according to the present invention, and the sample and the antibody react with each other so that a signal can be analyzed to diagnose the cancer. Here, the signal includes, but not limited to, antibody conjugated enzyme, for example, alkaline phosphatase, β-galactosidase, horseradish peroxidase, luciferase or cytochrome P450. Where alkaline phosphatase is used as the enzyme, bromochloroindolylphosphate (BCIP), nitro blue tetrazolium (NBT), naphthol-AS-B1-phosphate and ECF (enhanced chemifluorescence) may be used as a substrate for color-developing reactions. In the case of using horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (tetramethylbenzidine), ABTS (2,2-Azine-di[3-ethylbenzthiazoline sulfonate]), o-phenylenediamine (OPD) and naphtol/pyronine may be used as a substrate; and in the case of using glucose oxidase, t-NBT (nitroblue tetrazolium) or m-PMS (phenzaine methosulfate) may be used as a substrate. The scope of the present invention is not limited thereto.

In addition, the kit according to the present invention may include a label that generates a detectable signal. The label includes, but is not limited to, chemical substance (e.g., biotin), enzymes (alkaline phosphatase, β-galactosidase, horseradish peroxidase and cytochrome P450), radioactive material (e.g., $C^{14}$, $I^{125}$, $P^{32}$ and $S^{35}$) , fluorescent material (e.g., fluorescein), luminescent material, chemiluminescent material and FRET (fluorescence resonance energy transfer).

The measurement of the enzyme activity or the signal, which are used for diagnosis of a cancer, may be carried out in accordance with a variety of methods known in the art. This can analyze the expression level of EGFRvIII qualitatively or quantitatively.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1

Examination of Expression of EGFRvIII

Generally, in order to screen an antibody by a phage display technique, a target antigen protein is adsorbed onto an immunotube, and then only an antibody having an excellent binding affinity for the recombinant protein is selected by a biopanning technique. However, recombinant proteins undergo no conformational change, and thus if an antibody is screened using a protein expressed on the cell surface, which undergoes a conformational change, an antibody that recognizes the conformational change of the antigen can be developed. Accordingly, in the present invention, an antibody that specifically recognizes EGFRvIII was screened by a cell panning technique using glioblastoma multiforme (GBM) patient-derived cells having EGFRvIII.

First, glioblastoma multiforme patient-derived cells (437, 448, 464, and 626; NT352T1, 626, 780) were obtained from the Brain Avatar Tissue Bank of the Samsung Medical Center, Institute for Refractory Cancer Research, and used in experiments. Before the cell panning technique was performed, mutations and expression levels of EGFRvIII in the obtained patient-derived cells were analyzed by RT-PCR (Reverse Transcription Polymerase Chain Reaction) and Western blot analysis.

The results are shown in FIG. 1. Referring to FIG. 1, RNA and protein expressions of EGFRvIII were the highest in the cells of the 626 patients.

Example 2

Results of EGFRvIII Antibody Screening and Sequencing

Figure 2:
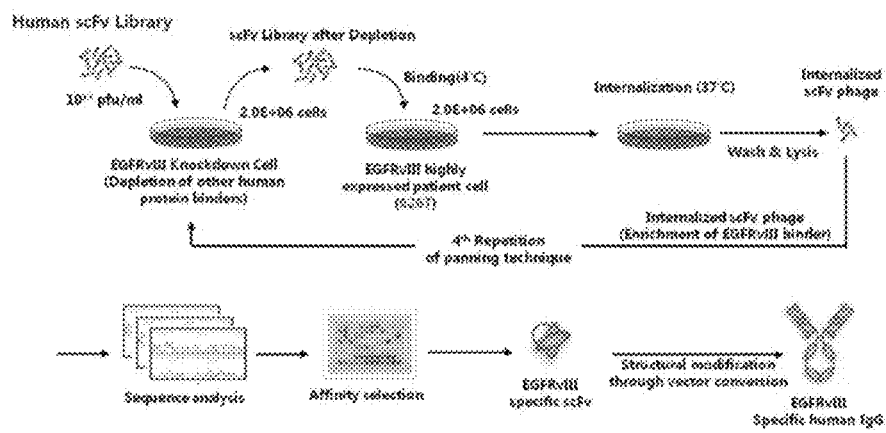
FIG. 2 shows a process of screening EGFRvIII-specific scFv antibody fragments by phage display.

For antibody screening, EGFRvIII-specific scFv antibody fragments were identified by phage display screening using a synthetic scFv phage library. The phage display screening process is shown in FIG. 2.

Specifically, to recover phagemid vectors, which include various human antibody genes introduced in E. coli host ER2537, by phage display, each of four synthetic scFv phage sub-library samples was added to 400 mL of a culture medium (SB/ampicillin/2% glucose) and cultured for about 2 hours. When the absorbance at OD600 reached 0.5, the cultured host cells were centrifuged at 5,000 g for 20 minutes, and the supernatant was removed, after which the cells were suspended in 400 mL of a second culture medium (SB/ampicillin), and then $10^{12}$ pfu (plaque forming unit) of helper phage (VCSM13) was added thereto, followed by culture for 1 hour. Next, a kanamycin antibiotic (an antibiotic gene introduced in helper phage) was added thereto at a concentration of 70 μg/mL, and then the cells were cultured overnight at 30° C. and 220 rpm so that a phage library could be made outside the host cells. Next, the culture was centrifuged, and PEG 8000 (polyethylene glycol 8000) was added to the supernatant which was then stirred at 4° C. for 2 hours so that the phage particles would be mixed well with PEG 8000. The stirred material was centrifuged at 15000 g and 4° C. for 30 minutes, and the precipitated pellets were suspended in 1 ml of PBS. The suspension was centrifuged at 10000 g and 4° C., and the supernatant was collected, thereby recovering phage libraries. In order to count the phages recovered from each sub-library, each sample was diluted, and host cells (ER2537) were infected with the dilution, followed by counting on LB/ampicillin solid medium.

Phage display screening was performed through repeated rounds of panning. The counted sub-libraries were collected to about $1.0 \times 10^{13}$ pfu, and then the EGFRvIII antigen-knockdown cells from the 626 glioblastoma multiforme patients were treated with each sub-library and incubated at 4° C. for 1 hour. The supernatant not bound to the EGFRvIII antigen-knockdown 626 patient cells was collected. This is a step of preventing non-specific binding to proteins other than EGFRvIII by removing phages, which bind to cell membrane proteins other than EGFRvIII, from the antibody phage library. After the supernatant was collected, the 626 (EGFRvIII+) patient-derived cells were treated with the supernatant and incubated at 4° C. for 1 hour. The cells were treated five times with cold complete medium to remove non-specific binding, and then incubated at 37° C. for 30 minutes, thereby inducing receptor-mediated internalization of an antigen-antibody complex. The cells were washed with cold PBS and finally washed with 0.1M glycine buffer (pH 2.0), thereby removing non-cell-internalized phage particles bound to the cell surface. The cells were neutralized with 2M Tris buffer (pH 8.0), and lysed by incubation with 0.5 ml of 100 mM TEA (triethylamine) for 10 minutes, and then neutralized with 1 mL of 2M Tris buffer (pH 8.0). After ER2537 E. coli strain cultured to OD600=0.5-0.8 was previously prepared, 1.5 mL of the neutralized recovered phage solution was added to 8.5 mL of the ER2537 E. coli strain culture, and the ER2537 E. coli strain was infected with the recovered phages by incubation at 37° C. and 120 rpm for 1 hour, followed by counting on LB/ampicillin solid medium. The remaining recovered solution was plated and incubated on 15 cm LB/ampicillin solid medium, and then 5 mL of SB medium (50% glycerol) was added thereto, and colonies were recovered and stored (−80° C.)

Figure 3:
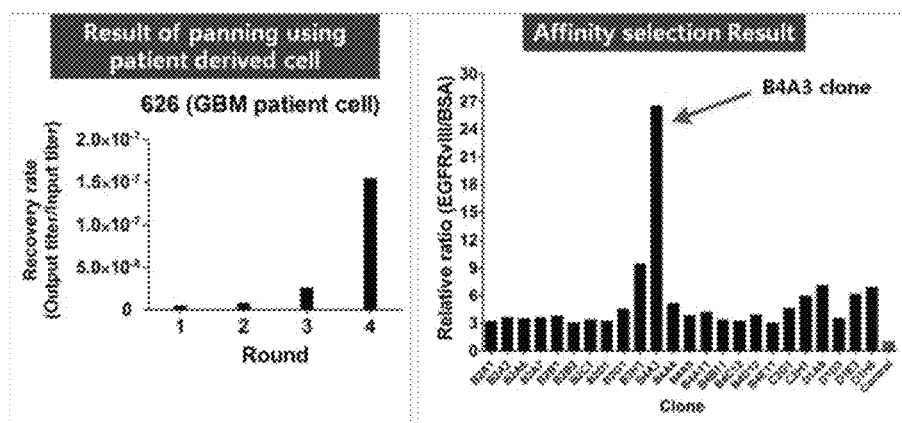
FIG. 3 shows the results of screening EGFRvIII antibody using GBM patient-derived cells and the results of sequencing.

For subsequent panning rounds, 50 μL of the stored phage solution resulting from the previous round of panning was taken and subjected to phage particle amplification. Helper phages (VCSM13) were added to host cells after culture, and the phage particles were recovered through PEG precipitation with PEG 8000. Using the recovered phage particles, the next round of panning was performed in the same manner as the previous round of panning. Panning was performed for a total of four rounds on the 626 (EGFRvIII+) patient-derived cells, and the phage display screening results are shown in FIG. 3 and Table 1 below.

TABLE 1

| Round | Input (cfu/mL) | Output (cfu/mL) | Recovery rate (Output/Input) |
|---|---|---|---|
| 1 | 1E+13 | 4.85E+4 | 4.85E−9 |
| 2 | 1.13E+13 | 8.96E+4 | 7.93E−9 |
| 3 | 9.32E+12 | 2.43E+5 | 2.61E−8 |
| 4 | 6.97E+12 | 1.08E+6 | 1.55E−7 |

For each round of cell panning, recovery rate was measured by the ratio of phage particles, recovered after binding to the 626-patient cells and internalization into the cells, to phage particles added for cell panning. It was shown that, as the number of rounds of the patient-derived cell panning increased, the ratio of recovered phage particles (output) to phage particles (input) added to the 626 cells increased, indicating that target-specific binders tended to be enriched. After completion of a total of four rounds of cell panning on the 626-patient cells, the phage particles recovered in the final round (round 4) were identified as colonies on an LB/ampicillin plate through infection of host cells (ER2537).

The colonies were collected, and each colony was inoculated into each well of a 96-well plate containing 200 μL of SB/ampicillin medium, followed by incubation (at 37° C. for about 3 hours). Next, in order to induce expression of the scFv-pIII protein, each well was treated with 1 mM of IPTG and incubated overnight at 30° C. Then, the culture plate was centrifuged, and the supernatant was removed. Next, to recover a periplasm fraction from the cultured cells in each well, each well was treated with 40 μL of TES solution (20% w/v sucrose, 50 mM Tris, 1 mM EDTA, pH 8.0) maintained at 4° C., after which it was incubated at 4° C. for 30 minutes, treated with 60 μL of 0.2× TES solution, and then incubated for 30 minutes. Finally, the plate was centrifuged, and the supernatant was recovered, thereby producing the scFv-pIII protein in a small scale.

Meanwhile, each of EGFRvIII protein and BSA was coated on 96-well plates at a concentration of 1 μg/mL and blocked with 3% skimmed milk powder, after which 25 μL of the recovered periplasm fraction was taken and added to each well of the plates coated with each of EGFRvIII and BSA, followed by incubation for 1 hour. Next, each well was washed with 3-4 times with TBST, and incubated with HRP-conjugated anti-HA antibody (12013819001, Roche Life Science) for 1 hour. Next, each well was washed again, and color development reaction (TMB substrate) was induced, after which the O.D. values at 450 nm were measured. The O.D. value at 450 nm, obtained by treating the EGFRvIII antigen-coated plate with any scFv-pIII, was divided by the O.D 450 nm value obtained by treating the BSA antigen-coated plate with scFv-pIII, and scFv candidates showing a binding affinity for EGFRvIII were selected.

752 colonies were analyzed, and as a result, 24 clones (affinity multiple>3) showed a tendency to bind to EGFRvIII. Two clones (B3H1 and B4A3) did bind more strongly than other antibody clones, and among them, B4A3 showed the highest binding affinity. The B4A3 clone showing a specifically high affinity for the EGFRvIII antigen was finally selected, and the amino acid sequence of the B4A3 clone is shown in Table 2 below.

TABLE 2

|  | Heavy chain | Light chain |
|---|---|---|
| CDR1 | GFTFSNYY (SEQ ID NO: 2) | SSNIGNNY (SEQ ID NO: 5) |
| CDR2 | TSPNGGSK (SEQ ID NO: 3) | SDS (SEQ ID NO: 6) |
| CDR3 | AKGRRKLRATRFDY (SEQ ID NO: 4) | ATWDASLSAYV (SEQ ID NO: 7) |

Example 3

Examination of the Specificity of B4A3 Antibody for EGFRvIII and Identification of Epitope To examine the binding affinity and function of an scFv antibody fragment alone, a B4A3 antibody fragment was expressed in a protein-expressing strain (TOP10F'). The B4A3 scFv protein was prepared through His-tag purification with Ni-NTA beads.

Figure 4:
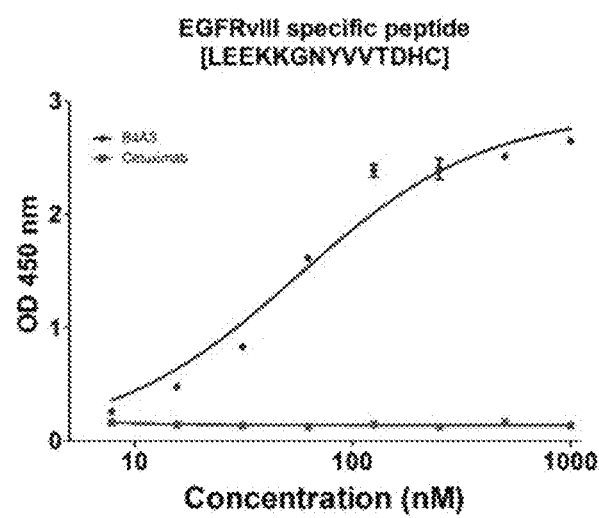
FIG. 4 shows the binding pattern of B4A3 antibody and Cetuximab for an EGFRvIII-specific peptide.
Figure 5:
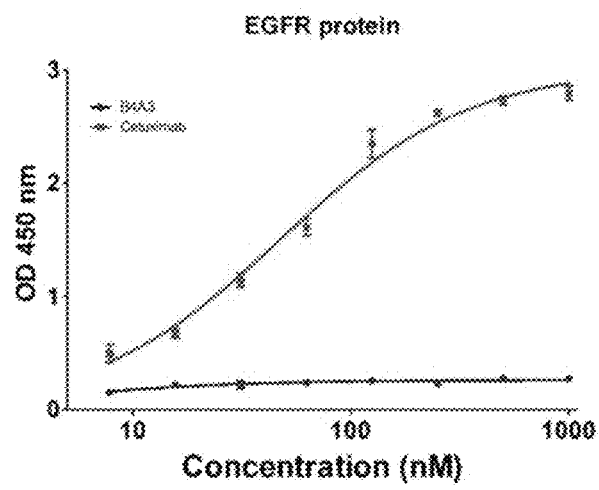
FIG. 5 shows the binding pattern of B4A3 antibody and Cetuximab for an EGFR recombinant protein.
Figure 6:
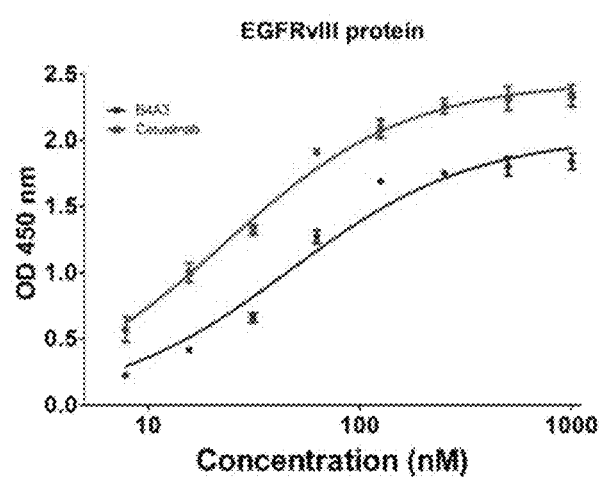
FIG. 6 shows the binding pattern of B4A3 antibody and Cetuximab for an EGFRvIII recombinant protein.

To examine the specificity of the produced scFv protein for EGFRvIII, ELISA was performed to analyze the binding patterns of the scFv protein for a peptide (LEEKKGNYV-VTDHC), an EGFRvIII recombinant protein and an EGFR recombinant protein, which are specific only for EGFRvIII mutants. The results are shown in FIGS. 4 to 6.

As a comparative antibody for the binding patterns, Cetuximab known as an EGFR antibody was used. Cetuximab binds to both the EGFR protein and the EGFRvIII protein, because it binds to the domain III (L2) of the EGFR protein and this domain is also present in the EGFRvIII protein. It was shown that Cetuximab did bind to both the EGFR recombinant protein and the EGFRvIII recombinant protein, but did not bind to the LEEKKGNYVVTDHC sequence which is absent in EGFR and present specifically in EGFRvIII. This is because Cetuximab recognizes the L2 domain (aa 310-480) of EGFR as an epitope and this domain is present commonly in EGFR and EGFRvIII. However, it was shown that the B4A3 antibody did bind to the LEEK-KGNYVVTDHC sequence present specifically in the EGFRvIII recombinant protein and EGFRvIII, but did not substantially bind to the EGFR recombinant protein. This suggests that the B4A3 antibody fragment recognizes, as an epitope, LEEKKGNYVVTDHC (SEQ ID NO: 1) which is the N-terminal amino acid sequence (residues 1 to 14) of the EGFRvIII protein.

In addition, using ELISA, the concentration-dependent affinities of B4A3 (which is anti-EGFRvIII scFv) for the EGFRvIII-specific peptide and the EGFRvIII recombinant protein were measured. Based on the results of ELISA performed in triplicate, the apparent affinities of the B4A3 scFv protein for the EGFRvIII peptide and the EGFRvIII recombinant protein were examined using Prism program and nonlinear regression analysis. As a result, it was shown that the B4A3 scFv showed an apparent affinity of 0.2715 nM for the EGFRvIII-specific peptide, and an apparent affinity of 2.347 nM for the EGFRvIII recombinant protein.

TABLE 3

| Antibody analyzed | Antigen | $K_a$ | $K_d$ | $K_D$ (nM) |
|---|---|---|---|---|
| B4A3 scFv | EGFRvIII peptide (LEEKKGNYVVTDHC) | 3.541e+006 | 0.0009613 | 0.2715 |
|  | rhEGFRvIII protein | 2.739e+006 | 0.006430 | 2.347 |

In order to examine whether the B4A3 antibody fragment (scFv) can specifically recognize EGFRvIII, Western blot analysis was performed. The 626 glioblastoma multiforme patient cells having the EGFRvIII mutant were lysed, thereby obtaining a protein from the 626-patient cells.

Figure 7:
FIG. 7 shows the results of SDS-PAGE performed to examine the binding specificity of B4A3 antibody for EGFRvIII after staining with B4A3 antibody and EGFR control antibody.

30 μg of the protein from the 626-patient cells was loaded on SDS-PAGE gel which was then transferred to a PVDF membrane, followed by staining with the B4A3 antibody clone (primary antibody) and EGFR control antibody (#4267, Cell Signaling Technology, Inc.). As a result, it was shown that the B4A3 antibody clone could bind specifically to EGFRvIII (FIG. 7).

Example 4

Figure 8:
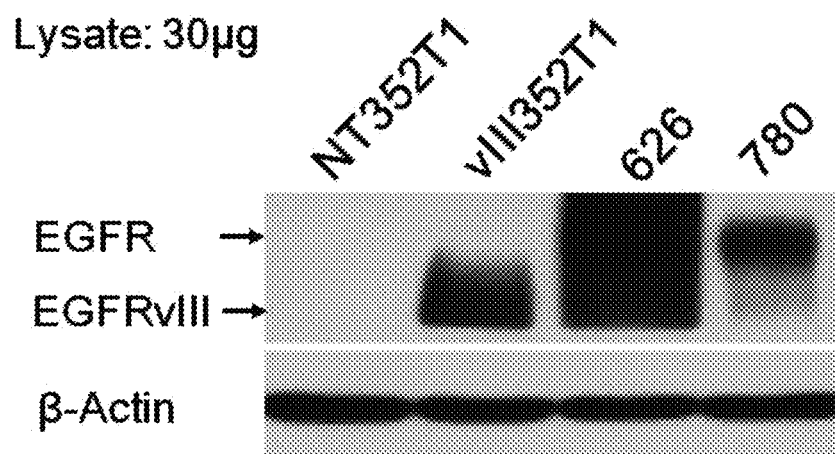
FIG. 8 shows the results of Western blot analysis performed to examine the expression patterns of EGFR and EGFRvIII.

Examination of Binding Specificity of Anti-EGFRvIII scFv Using EGFRvIII-Overexpressing Cells Glioblastoma multiforme patient-derived cells (NT352T1, 626, 780) were obtained from the Brain Avatar Tissue Bank of the Samsung Medical Center, Institute for Refractory Cancer Research, and used in experiments. To construct cells that express only EGFRvIII, an EGFRvIII overexpression vector was introduced into NT352T1 cells free of EGFR and EGFRvIII, thereby making vIII352T1 cells which were used in a subsequent experiment. To examine the expression patterns of EGFR and EGFRvIII, the cells from each patient were lysed, and then 30 μg of the protein lysate was analyzed by Western blot analysis. The results are shown in FIG. 8. As primary antibody, EGFR rabbit mAb (#4267, Cell Signaling Technology, Inc.) was used, and as secondary antibody, anti-rabbit IgG, HRP-linked antibody (#7074, Cell Signaling Technology, Inc.) was used. The results of analyzing the expression patterns of EGFR and EGFRvIII in the patient cells are shown in Table 4 below.

TABLE 4

Results of analysis of expression patterns of EGFR and EGFRvIII in patient cells

| Cells | EGFRvIII | EGFR |
|---|---|---|
| Nt352T1 | − | − |
| vIII352T1 | + | − |
| 626 | + | + |
| 780 | − | + |

Figure 9:
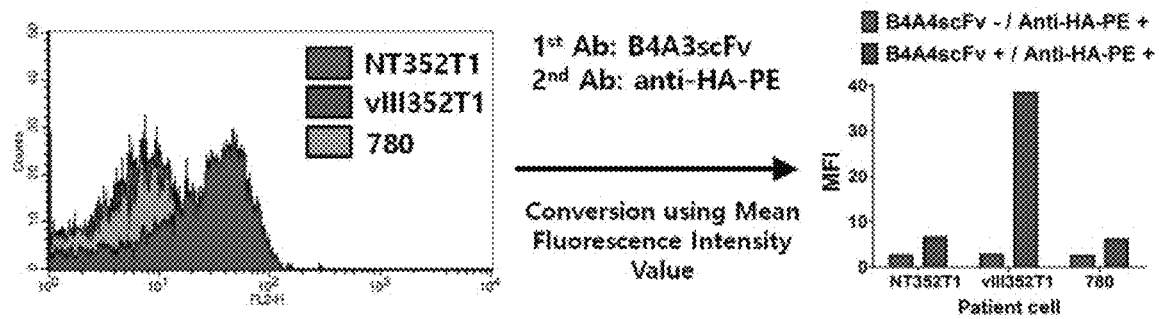
FIG. 9 shows the results of FACS analysis performed to analyze the binding pattern of anti-EGFRvIII scFv to EGFRvIII in cells.

In order to analyze the binding pattern of anti-EGFRvIII scFv to EGFRvIII in glioblastoma multiforme patient cells, FACS analysis was performed. NT352T1 patient cells hardly express EGFR and EGFRvIII. In vIII352T1 obtained by expressing EGFRvIII in the NT352T1 patient cells, only the EGFRvIII protein is expressed, and EGFR is not expressed. The 626-patient cells have both EGFRvIII and EGFR, and the 780-patient cells express only EGFR and have no EGFRvIII mutant. NT352T1(EGFR−/EGFRvIII−), vIII352T1(EGFR−/EGFRvIII+), 780(EGFR+/EGFRvIII−) The patient cells were cultured in medium (NBA), and the cultured cells were placed in each tube at a density of 5 ×10$^5$ cells. Next, the cells were fixed with 4% paraformaldehyde, centrifuged, and then washed once with FACS analysis solution. The prepared cells were treated with 1 1 μg of B4A3 scFv (which is anti-EGFRvIII scFv), and then incubated overnight at 4° C. so that the antibody fragment would bind to the cells. Next, non-specifically bound scFv protein was removed by washing twice with FACS solution, and the cells were incubated with fluorescence (PE, phycoerythrin)-labeled anti-HA antibody (sc-805 PE, Santa Cruz Biotechnology, Inc.) for 1 hour. The cells were washed again with FACS solution, and 500 μL of FACS solution was added thereto, followed by FACS analysis. As a result, as shown in FIG. 9, B4A3 scFv (which is anti-EGFRvIII scFv) showed the ability to bind specifically to the vIII352T1 patient cells having only EGFRvIII. It was shown that B4A3 scFv did not bind to the NT352T1 patient cells having neither EGFR nor EGFRvIII and to the 780-patient cells having only EGFR. This suggests that the identified EGFRvIII scFv antibody has specificity for the extracellular region of EGFRvIII present in the actual cell membrane.

Example 5

Verification of Specificity of Anti-EGFRvIII IgG1

Figure 10:
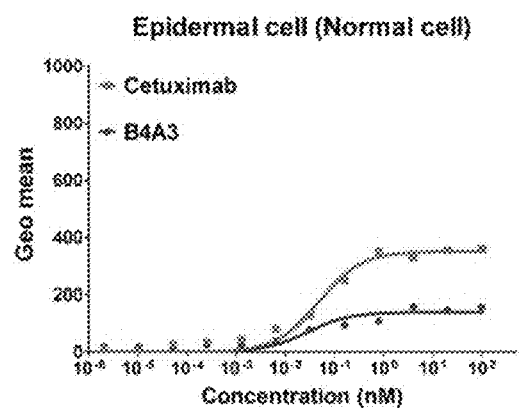
FIG. 10 shows the results of analyzing the binding pattern of B4A3 antibody (IgG1) in normal cells.
Figure 11:
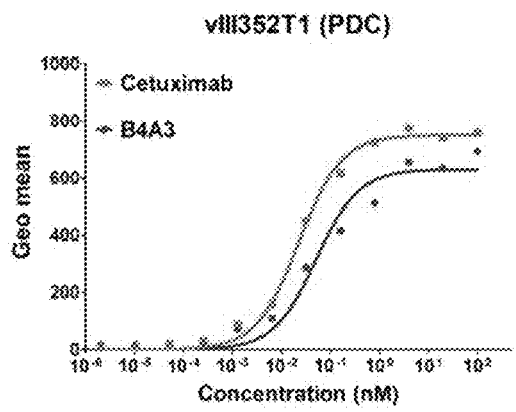
FIG. 11 shows the results of analyzing the binding pattern of B4A3 antibody (IgG1) in vIII352T1 that expresses only EGFRvIII.

Using normal cells that express EGFR and the vIII352T1 cells that express EGFRvIII, the specificity of the B4A3 EGFRvIII antibody was verified. The B4A3 antibody used in FACS analysis was used after conversion to B4A3 human IgG1 type. Normal epidermal cells [Primary Epidermal Keratinocytes; Normal, Human, Adult (ATCC® PCS-200-011m)] that express only EGFR were purchased from the ATCC and used. FACS analysis was performed in the same manner as mentioned above. As primary antibody, each of Cetuximab and B4A3 IgG was used, and as secondary antibody, Alexa Fluor 488 Goat Anti-Human IgG (H+L) Antibody (Life Technologies) was used. Based on the above results, it was shown that the B4A3 antibody (IgG1) did bind specifically to vIII352T1 cells that express only EGFRvIII (FIG. 11), while the binding of the B4A3 antibody to the normal cells was minimized compared to that of the control antibody cetuximab (FIG. 10). Based on the minimized affinity for the normal cells, the B4A3 antibody appears to show minimized cytotoxicity against the normal cells.

Example 6

Cytotoxicity of Toxin-Conjugated EGFRvIII Antibody

Figure 12:
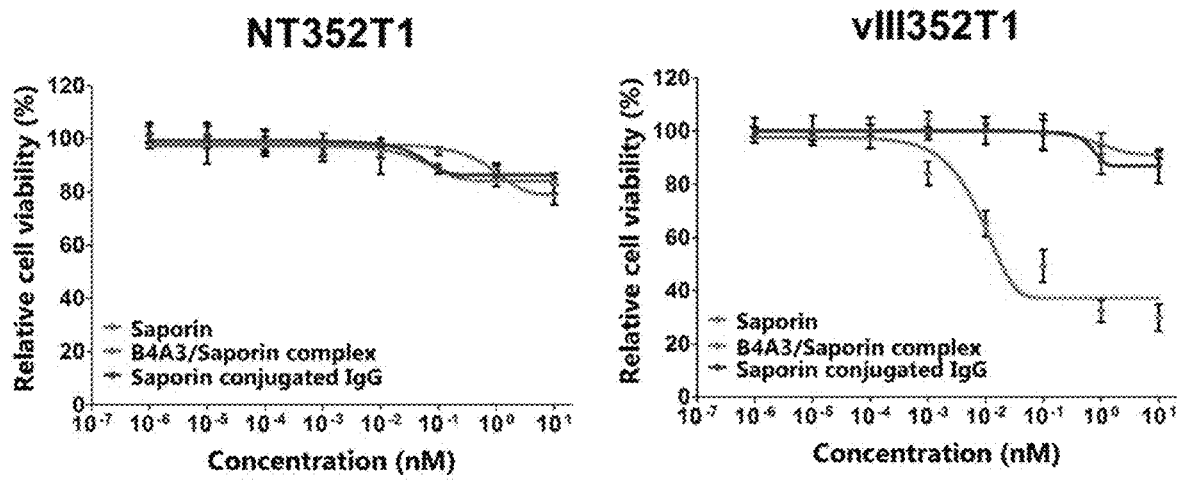
FIG. 12 shows results indicating that an EGFRvIII-specific antibody/saporin conjugated antibody complex obtained by linking the saporin conjugated antibody to the B4A3 antibody is effectively internalized into EGFRvIII-expressing patient cells and, at the same time, induces cytotoxicity.

In order to verify whether the B4A3 antibody can be internalized into target cells by binding to the EGFRvIII/EGFR of the target cells and is applicable as antibody-drug conjugates, saporin was linked to the B4A3 antibody, and cytotoxicity assay was performed. Linking of saporin to the B4A3 antibody was performed using a ZAP antibody internalization kit (Advanced Targeting Systems, Inc.). The toxic substance saporin provided in the ZAP antibody internalization kit is a substance conjugated to anti-human IgG-IgG and binds as secondary antibody to the human IgG B4A3 antibody. Saporin alone cannot enter cells, and a complex of B4A3 human IgG/saporin conjugated anti-human IgG-IgG is internalized into cells by binding to the target antigen EGFRvIII, and the saporin is released into the cells and induces cytotoxicity by inactivating ribosomes. Because saporin conjugated anti-human IgG-IgG does not bind to the surface of general cells, including patient-derived cells and the like, it does not cause cytotoxicity by itself. The experiment was performed according to the protocol provided by the kit manufacturer. Specifically, NT352T1 patient cells expressing no EGFRvIII and vIII352T1 patient cells expressing EGFRvIII were dispensed into each well of 96-well cell culture plates at a density of 5000 cells/well in an amount of 90 μl. On the next day, the cell culture medium was treated with 10 μl of the B4A3 human IgG/saporin conjugated anti-human IgG-IgG complex, and the B4A3 antibody was diluted 10-fold from the highest concentration of 10 nM to make 8 concentrations. The experiment was performed in triplicate at the 8 antibody concentrations. In order to examine whether cytotoxicity would be antibody-specific, a group treated with saporin alone and a group treated with saporin conjugated anti-human IgG-IgG were additionally used as control groups in the experiment. 72 hours after treatment with each of the complex and saporin, cell growth was analyzed. The analysis was performed using an EZ-Cytox kit (WST based Cell Viability/Cytotoxicity Assay Kit). After treatment with color development reagent, incubation was performed in a $CO_2$ incubator at 37° C. for 2 hours, and then OD value at 450 nm was analyzed. As a result, it was shown that in the NT352T1 cells that do not express the target antigen EGFRvIII, no cytotoxicity appeared, and in the vIII352T1 patient cells, the group treated with saporin alone and the group treated with saporin conjugated anti-human IgG-IgG showed no cytotoxicity, but the B4A3 IgG/saporin conjugated anti-human IgG-IgG group showed cytotoxicity (FIG. 12). This suggests that the B4A3 antibody is applicable as ADC (Antibody-Drug Conjugates).

Example 7

Quantification of the Affinities of B4A3 Antibody for EGFR and EGFRvIII

Figure 14:
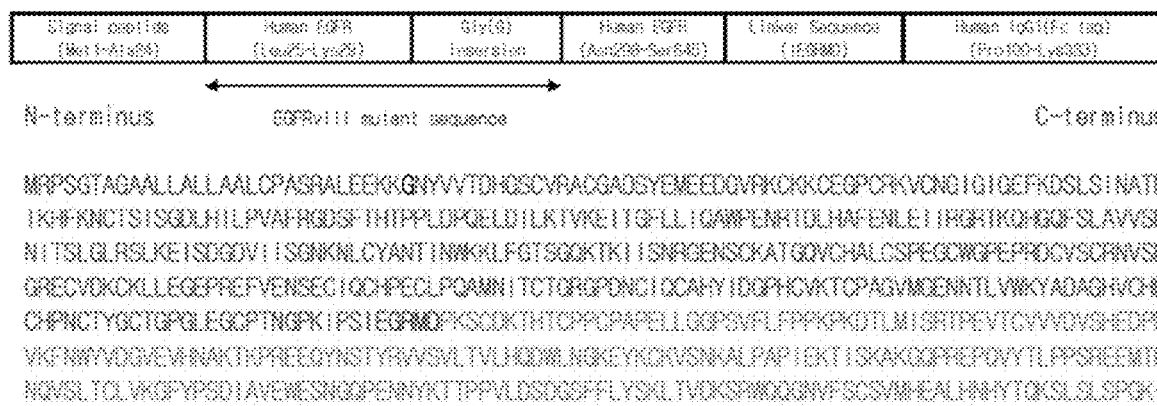
FIG. 14 shows a vector for producing recombinant EGFR and EGFRvIII to quantify the affinities of B4A3 antibody for EGFR and EGFRvIII.
Figure 15:
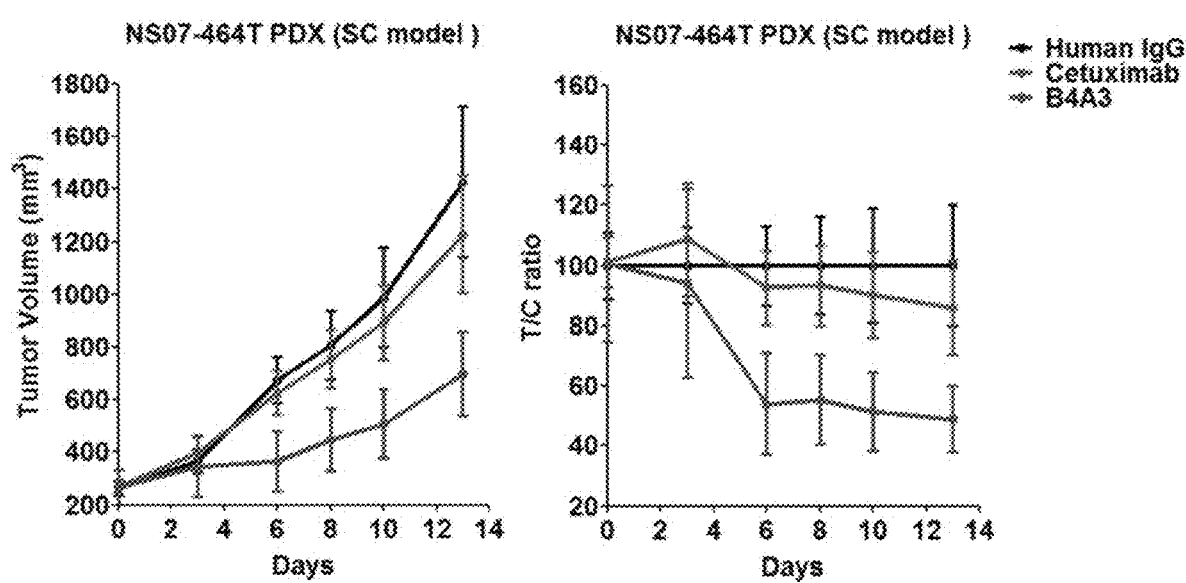
FIG. 15 shows the results of in vivo analysis to examine the ability of B4A3 to inhibit cancer cell growth.

To quantify the affinities of the B4A3 antibody for EGFR and EGFRvIII, SPR (Surface Plasmon Resonance)-based Biacore T200 (GE Healthcare Life Sciences) was used. The antigen EGFRvIII recombinant protein used to determine the affinities of the antibody was produced in-house. Based on the EGFR (Entry: P00533) sequence (www.uniprot.org) and with reference to the literature, the amino acid residues at positions 30 to 297 in the amino acid sequence of the extracellular domain of EGFR were removed, and then glycine amino acid was added between position 29 and position 298, and an Fc tag (Pro110-Lys330 of IgG1 CH2 and CH3 domains) was added to the C-terminus, thereby constructing a vector (SEQ ID NO: 20; FIG. 14). For use, the vector was produced/purified using animal cells (Expi293, Gibco). As the EGFR recombinant protein, a recombinant human EGFR/ErbB1 Fc chimera protein (R&D systems, 344-ER) was used.

Specifically, using Biacore T200 equipped with Series S Sensor Chip CM5 (GE Healthcare Life Sciences, BR100530), an amine coupling kit (GE Healthcare Life Sciences, BR100050) and a human Fab capture kit (GE Healthcare Life Sciences, 28-9583-25), human Fab capture antibody was immobilized on the sensor chip surface according to the manufacturer's manual. For affinity quantification, the B4A3 antibody was diluted in HBS-EP+ (GE Healthcare Life Sciences, BR100669) at a concentration of 10 μg/mL, added at a rate of 30 μl/min for 120 seconds, and then stabilized. The EGFRvIII antigen was diluted in HBS-EP+ (GE Healthcare Life Sciences, BR100669), and the concentration thereof was increased two-fold from 0.25 nM to 256 nM, and analysis was performed for each cycle. The antigen was diluted in HBS-EP+ at a predetermined concentration, and then associated at a rate of 30 μl/min for 180 seconds and dissociated by allowing HBS-EP+ solution to flow at a rate of 30 μl/min for 360 seconds. After completion of analysis at each concentration, the antibody and antigen used in the previous step were removed using glycine 2.0 regeneration buffer (GE Healthcare Life Sciences, BR100355), and the next analysis was performed. In the same manner as described above, quantification of the affinity for EGFR was performed, and the affinity of the antibody for the antigen was quantified using Biaevaluation software (GE Healthcare Life Sciences).

Figure 13:
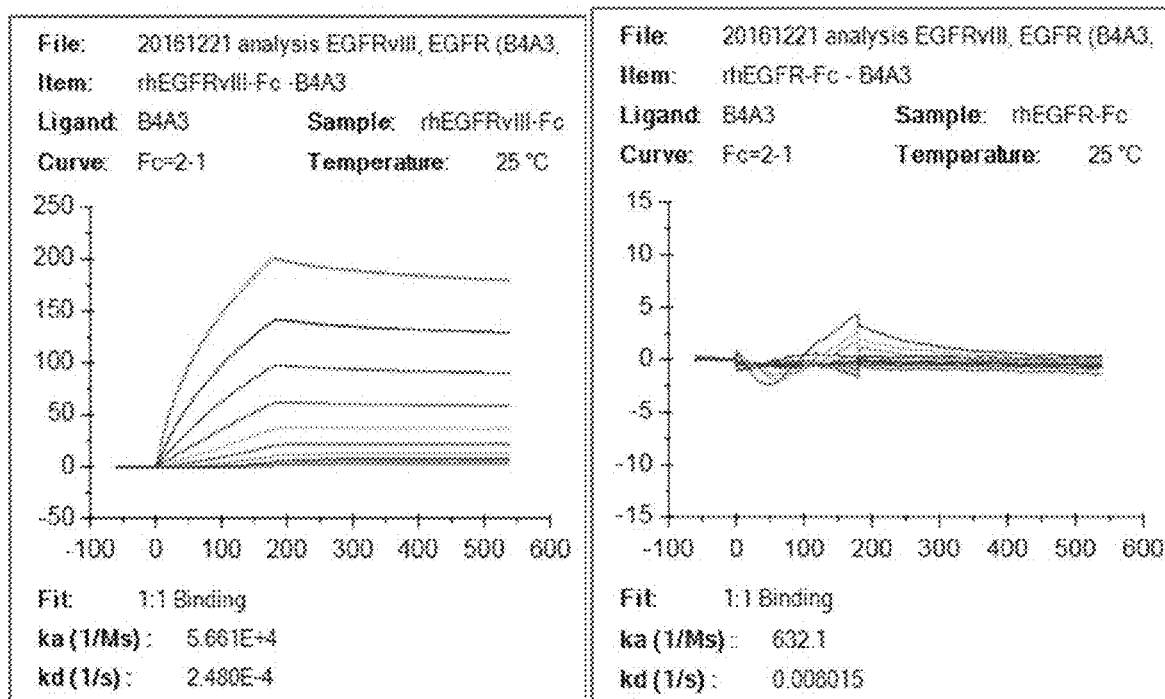
FIG. 13 shows the binding kinetics of B4A3 antibody.

It could be seen through Sensorgram that the B4A3 antibody did not substantially bind to the EGFR recombinant protein. It was shown that the association constant of the antibody for the EGFRvIII recombinant protein was $5.661 \times 10^4$ (1/Ms) and the dissociation constant was $2.480 \times 10^{-4}$ (1/s). Based on these results, it was determined that the B4A3 antibody did bind to EGFRvIII with an affinity of 4.38 nM (FIG. 13).

Example 8

Evaluation of Efficacy of B4A3 Antibody in In Vivo Model

In order to evaluate the in vivo efficacy of the B4A3 antibody against EGFR and EGFRvIII, NS07-464T cells among GBM patient-derived cells were used. The NS07-464T cells are GBM patient-derived cells that overexpress/amplify EGFR and have an EGFRvIII mutant. Based on gene data analyzed by the Samsung Medical Center, Institute for Refractory Cancer Research, NS07-464T cells were selected as EGFRvIII mutant cells. The NS07-464T cells were obtained from the Brain Avatar Tissue Bank of the Samsung Medical Center, Institute for Refractory Cancer Research, and used in experiments, the expression of EGFRvIII in the NS07-464T cells was analyzed by RT-PCR and Western blot analysis (FIG. 2). Using the NS07-464T patient cells, subcutaneous xenograft models were constructed. When a tumor having a volume of about 265 mm³ was formed, each of human IgG (Sigma, I4506), Cetuximab (Merck) and the B4A3 antibody was administered twice a week (a total of four times) at a dose of 10 mg/kg. Five mice were treated with each of human IgG and Cetuximab, and four mice were treated with B4A3. On 13 days after the start of administration of the antibody, and a tumor having a volume of 1426.5 mm³ was formed in the group treated with human IgG, and a tumor having a volume of 1228.5 mm³ was formed in the Cetuximab-treated group on day 13, indicating that the inhibition of tumor formation in the Cetuximab-treated group relative to tumor formation in the control group was 14%. In the group treated with the B4A3 antibody, a tumor having a volume of 699.5 mm³ was formed on 13 days of administration, indicating that the inhibition of tumor formation in the B4A3-treated group relative to tumor formation in the control group was 51%. This verifies that the B4A3 antibody exhibits excellent anticancer effects on patient-derived cells having an EGFRvIII mutant.

INDUSTRIAL APPLICABILITY

Features and advantages of the present invention are summarized as follows:

(i) The present invention provides an anti-EGFRvIII antibody, which is internalized into cancer cells after binding to EGFRvIII expressed on the surface of the cancer cells, and the pharmaceutical use of the antibody.

(ii) The antibody of the present invention inhibits the invasion and metastasis of cancer cells that express EGFRvIII.

(iii) The antibody of the present invention may be used for the treatment or diagnosis of cancer. Because EGFRvIII is a molecule which is expressed on the cell of cancer cells, the use of the antibody of the present invention can selectively target only cancer cells while having a minimal effect on normal cells.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. An antibody or antigen-binding fragment thereof binding to EGFRvIII (Epidermal Growth Factor Receptor Variant III), in which the antibody or antigen-binding fragment thereof binds to an EGFRvIII epitope having a sequence of SEQ ID NO: 1, comprising a heavy chain variable region comprising complementarity determining region (CDR) H1 comprising a sequence of SEQ ID NO: 2, CDRH2 comprising a sequence of SEQ ID NO: 3, and CDRH3 comprising a sequence of SEQ ID NO: 4; and
    a light chain variable region comprising CDRL1 comprising a sequence of SEQ ID NO: 5, CDRL2 comprising a sequence of SEQ ID NO: 6, and CDRL3 comprising a sequence of SEQ ID NO: 7.

2. The antibody or antigen-binding fragment thereof according to claim 1, wherein the antibody or antigen-binding fragment thereof comprises a framework region (FR) comprising one or more sequences selected from the group consisting of sequences of SEQ ID NOS: 8 to 15.

3. The antibody or antigen-binding fragment thereof according to claim 1, wherein the antibody or antigen-binding fragment thereof comprises a heavy chain variable region comprising a sequence of SEQ ID NO: 16.

4. The antibody or antigen-binding fragment thereof according to claim 1, wherein the antibody or antigen-binding fragment thereof comprises a light chain variable region comprising a sequence of SEQ ID NO: 17.

5. A kit comprising the antibody or antigen-binding fragment thereof according to claim 1, wherein the antibody or antigen-binding fragment is detectably labeled.

6. A composition comprising an antibody or antigen-binding fragment thereof binding to EGFRvIII (Epidermal Growth Factor Receptor Variant III) and a pharmaceutically acceptable carrier, wherein the antibody or antigen-binding fragment thereof binds to an EGFRvIII epitope having a sequence of SEQ ID NO: 1, comprising a heavy chain variable region comprising complementarity determining region (CDR) H1 comprising a sequence of SEQ ID NO: 2, CDRH2 comprising a sequence of SEQ ID NO: 3, and CDRH3 comprising a sequence of SEQ ID NO: 4; and a light chain variable region comprising CDRL1 comprising a sequence of SEQ ID NO: 5, CDRL2 comprising a sequence of SEQ ID NO: 6, and CDRL3 comprising a sequence of SEQ ID NO: 7.

* * * * *

UNITED STATES PATENT AND TRADEMARK OFFICE
CERTIFICATE OF CORRECTION

| | |
|---|---|
| PATENT NO. | : 10,669,340 B2 |
| APPLICATION NO. | : 16/073787 |
| DATED | : June 2, 2020 |
| INVENTOR(S) | : Do-Hyun Nam et al. |

It is certified that error appears in the above-identified patent and that said Letters Patent is hereby corrected as shown below:

In the Specification

Column 6, Lines 7 and 8: "WO88/10649" should be -- WO88/01649 --.

Column 6, Line 8: "WO88/106630" should be -- WO88/06630 --.

Signed and Sealed this
Seventh Day of July, 2020

Andrei Iancu
*Director of the United States Patent and Trademark Office*

SEQUENCE LISTING

<160> NUMBER OF SEQ ID NOS: 20

<210> SEQ ID NO 1
<211> LENGTH: 14
<212> TYPE: PRT
<213> ORGANISM: Artificial Sequence
<220> FEATURE:
<223> OTHER INFORMATION: EGFRvIII epitope

<400> SEQUENCE: 1

Leu Glu Glu Lys Lys Gly Asn Tyr Val Val Thr Asp His Cys
1               5                   10

<210> SEQ ID NO 2
<211> LENGTH: 8
<212> TYPE: PRT
<213> ORGANISM: Artificial Sequence
<220> FEATURE:
<223> OTHER INFORMATION: CDRH1 of B4A3

<400> SEQUENCE: 2

Gly Phe Thr Phe Ser Asn Tyr Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: CDRH2 of B4A3

<400> SEQUENCE: 3

Thr Ser Pro Asn Gly Gly Ser Lys
1               5

<210> SEQ ID NO 4
<211> LENGTH: 14
<212> TYPE: PRT
<213> ORGANISM: Artificial Sequence
<220> FEATURE:
<223> OTHER INFORMATION: CDRH3 of B4A3

<400> SEQUENCE: 4

Ala Lys Gly Arg Arg Lys Leu Arg Ala Thr Arg Phe Asp Tyr
1               5                   10

<210> SEQ ID NO 5
<211> LENGTH: 8
<212> TYPE: PRT
<213> ORGANISM: Artificial Sequence
<220> FEATURE:
<223> OTHER INFORMATION: CDRL1 of B4A3

<400> SEQUENCE: 5

Ser Ser Asn Ile Gly Asn Asn Tyr
1               5

<210> SEQ ID NO 6
<211> LENGTH: 3
<212> TYPE: PRT
<213> ORGANISM: Artificial Sequence
<220> FEATURE:
<223> OTHER INFORMATION: CDRL2 of B4A3

<400> SEQUENCE: 6

Ser Asp Ser
1

```
<210> SEQ ID NO 7
<211> LENGTH: 11
<212> TYPE: PRT
<213> ORGANISM: Artificial Sequence
<220> FEATURE:
<223> OTHER INFORMATION: CDRL3 of B4A3

<400> SEQUENCE: 7

Ala Thr Trp Asp Ala Ser Leu Ser Ala Tyr Val
1               5                   10

<210> SEQ ID NO 8
<211> LENGTH: 25
<212> TYPE: PRT
<213> ORGANISM: Artificial Sequence
<220> FEATURE:
<223> OTHER INFORMATION: Hv FR1 of B4A3

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 9
<211> LENGTH: 17
<212> TYPE: PRT
<213> ORGANISM: Artificial Sequence
<220> FEATURE:
<223> OTHER INFORMATION: Hv FR2 of B4A3

<400> SEQUENCE: 9

Met Ser Trp Val Arg Gln Ala Pro Gly Lys Gly Leu Glu Trp Val Ser
1               5                   10                  15

Gly

<210> SEQ ID NO 10
<211> LENGTH: 38
<212> TYPE: PRT
<213> ORGANISM: Artificial Sequence
<220> FEATURE:
<223> OTHER INFORMATION: Hv FR3 of B4A3

<400> SEQUENCE: 10

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
                35

<210> SEQ ID NO 11
<211> LENGTH: 11
<212> TYPE: PRT
<213> ORGANISM: Artificial Sequence
<220> FEATURE:
<223> OTHER INFORMATION: Hv FR4 of B4A3

<400> SEQUENCE: 11

Trp Gly Gln Gly Thr Leu Val Thr Val Ser Ser
1               5                   10

<210> SEQ ID NO 12
```

-continued

<211> LENGTH: 25
<212> TYPE: PRT
<213> ORGANISM: Artificial Sequence
<220> FEATURE:
<223> OTHER INFORMATION: Lv FR1 of B4A3

<400> SEQUENCE: 12

Gln Ser Val Leu Thr Gln Pro Pro Ser Ala Ser Gly Thr Pro Gly Gln
1               5                   10                  15
Arg Val Thr Ile Ser Cys Thr Gly Ser
            20                  25

<210> SEQ ID NO 13
<211> LENGTH: 17
<212> TYPE: PRT
<213> ORGANISM: Artificial Sequence
<220> FEATURE:
<223> OTHER INFORMATION: Lv FR2 of B4A3

<400> SEQUENCE: 13

Val Ser Trp Tyr Gln Gln His Pro Gly Thr Ala Pro Lys Leu Leu Ile
1               5                   10                  15
Tyr

<210> SEQ ID NO 14
<211> LENGTH: 36
<212> TYPE: PRT
<213> ORGANISM: Artificial Sequence
<220> FEATURE:
<223> OTHER INFORMATION: Lv FR3 of B4A3

<400> SEQUENCE: 14

Asn Arg Pro Ser Gly Val Pro Asp Arg Phe Ser Gly Ser Lys Ser Gly
1               5                   10                  15
Thr Ser Ala Ser Leu Ala Ile Ser Gly Leu Arg Ser Glu Asp Glu Ala
            20                  25                  30
Asp Tyr Tyr Cys
        35

<210> SEQ ID NO 15
<211> LENGTH: 10
<212> TYPE: PRT
<213> ORGANISM: Artificial Sequence
<220> FEATURE:
<223> OTHER INFORMATION: Lv FR4 of B4A3

<400> SEQUENCE: 15

Phe Gly Gly Gly Thr Lys Leu Thr Val Leu
1               5                   10

<210> SEQ ID NO 16
<211> LENGTH: 121
<212> TYPE: PRT
<213> ORGANISM: Artificial Sequence
<220> FEATURE:
<223> OTHER INFORMATION: Hv of B4A3

<400> SEQUENCE: 16

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Tyr Met Ser Trp Val Arg Gln Ala Pro Gly Lys Gly Leu Glu Trp Val
        35                  40                  45

Ser Gly Thr Ser Pro Asn Gly Gly Ser Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Arg Arg Lys Leu Arg Ala Thr Arg Phe Asp Tyr Trp Gly
            100                 105                 110

Gln Gly Thr Leu Val Thr Val Ser Ser
            115                 120

<210> SEQ ID NO 17
<211> LENGTH: 110
<212> TYPE: PRT
<213> ORGANISM: Artificial Sequence
<220> FEATURE:
<223> OTHER INFORMATION: Lv of B4A3

<400> SEQUENCE: 17

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Tyr Val Ser Trp Tyr Gln Gln His Pro Gly Thr Ala Pro Lys Leu Leu
        35                  40                  45

Ile Tyr Ser Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Thr Trp Asp Ala Ser Leu
                 85                  90                  95

Ser Ala Tyr Val Phe Gly Gly Gly Thr Lys Leu Thr Val Leu
            100                 105                 110

<210> SEQ ID NO 18
<211> LENGTH: 363
<212> TYPE: DNA
<213> ORGANISM: Artificial Sequence
<220> FEATURE:
<223> OTHER INFORMATION: Hv of B4A3

<400> SEQUENCE: 18
gaggtgcagc tgttggagtc tgggggaggc ttggtacagc ctggggggtc cctgagactc      60
tcctgtgcag cctctggatt caccttttagc aattattata tgagctgggt ccgccaggct    120
ccagggaagg gctggagtg gtctcaggg acctctccta atggtggtag taaatattac       180
gctgattctg taaaaggtcg gttcaccatc tccagagaca attccaagaa cacgctgtat    240
ctgcaaatga acagcctgag agccgaggac acggccgtgt attactgtgc gaaaggtcgt    300
cgtaagctgc gggctactcg gttcgactac tggggccagg gtacactggt caccgtgagc    360
tca                                                                   363

<210> SEQ ID NO 19
<211> LENGTH: 330
<212> TYPE: DNA
<213> ORGANISM: Artificial Sequence
<220> FEATURE:
<223> OTHER INFORMATION: Lv of B4A3

<400> SEQUENCE: 19

```
cagtctgtgc tgactcagcc accctcagcg tctgggaccc ccgggcagag ggtcaccatc    60
tcttgtactg gctcttcatc taatattggc aataattatg tctcctggta ccagcagcac   120
ccaggaacgg cccccaaact cctcatctat tctgatagta atcggccaag cggggtccct   180
gaccgattct ctggctccaa gtctggcacc tcagcctccc tggccatcag tgggctccgg   240
tccgaggatg aggctgatta ttactgtgct acttgggatg ctagcctgag tgcttatgtc   300
ttcggcggag gcaccaagct tacggtccta                                    330
```

<210> SEQ ID NO 20
<211> LENGTH: 615
<212> TYPE: PRT
<213> ORGANISM: Artificial Sequence
<220> FEATURE:
<223> OTHER INFORMATION: Recombinant EGFR EGFRvIII

<400> SEQUENCE: 20

```
Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Leu Leu Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
        195                 200                 205

Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Lys Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
```

```
                        290                 295                 300
Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                    325                 330                 335

Asn Thr Leu Val Trp Lys Tyr Ala Asp Ala Gly His Val Cys His Leu
                    340                 345                 350

Cys His Pro Asn Cys Thr Tyr Gly Cys Thr Gly Pro Gly Leu Glu Gly
                355                 360                 365

Cys Pro Thr Asn Gly Pro Lys Ile Pro Ser Ile Glu Gly Arg Met Asp
                370                 375                 380

Pro Lys Ser Cys Asp Lys Thr His Thr Cys Pro Pro Cys Pro Ala Pro
385                 390                 395                 400

Glu Leu Leu Gly Gly Pro Ser Val Phe Leu Phe Pro Pro Lys Pro Lys
                    405                 410                 415

Asp Thr Leu Met Ile Ser Arg Thr Pro Glu Val Thr Cys Val Val Val
                420                 425                 430

Asp Val Ser His Glu Asp Pro Glu Val Lys Phe Asn Trp Tyr Val Asp
                435                 440                 445

Gly Val Glu Val His Asn Ala Lys Thr Lys Pro Arg Glu Glu Gln Tyr
                450                 455                 460

Asn Ser Thr Tyr Arg Val Val Ser Val Leu Thr Val Leu His Gln Asp
465                 470                 475                 480

Trp Leu Asn Gly Lys Glu Tyr Lys Cys Lys Val Ser Asn Lys Ala Leu
                    485                 490                 495

Pro Ala Pro Ile Glu Lys Thr Ile Ser Lys Ala Lys Gly Gln Pro Arg
                500                 505                 510

Glu Pro Gln Val Tyr Thr Leu Pro Pro Ser Arg Glu Glu Met Thr Lys
                515                 520                 525

Asn Gln Val Ser Leu Thr Cys Leu Val Lys Gly Phe Tyr Pro Ser Asp
530                 535                 540

Ile Ala Val Glu Trp Glu Ser Asn Gly Gln Pro Glu Asn Asn Tyr Lys
545                 550                 555                 560

Thr Thr Pro Pro Val Leu Asp Ser Asp Gly Ser Phe Phe Leu Tyr Ser
                    565                 570                 575

Lys Leu Thr Val Asp Lys Ser Arg Trp Gln Gln Gly Asn Val Phe Ser
                580                 585                 590

Cys Ser Val Met His Glu Ala Leu His Asn His Tyr Thr Gln Lys Ser
                595                 600                 605

Leu Ser Leu Ser Pro Gly Lys
610                 615
```